US006434542B1

(12) United States Patent
Farmen et al.

(10) Patent No.: US 6,434,542 B1
(45) Date of Patent: Aug. 13, 2002

(54) STATISTICAL DECONVOLUTING OF MIXTURES

(75) Inventors: Mark W. Farmen, Martinsville, IN (US); Christophe Gerard Lambert, Emigrant, MT (US); Andrew R. Rusinko, III, Arlington, TX (US); Sidney Stanley Young, Raleigh, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/403,163

(22) PCT Filed: Apr. 17, 1998

(86) PCT No.: PCT/US98/07899

§ 371 (c)(1),
(2), (4) Date: Jan. 19, 2000

(87) PCT Pub. No.: WO98/47087

PCT Pub. Date: Oct. 22, 1998

Related U.S. Application Data (60) Provisional application No. 60/044,056, filed on Apr. 17, 1997.

(51) Int. Cl.$^7$ .............................................. G06F 9/445
(52) U.S. Cl. ........................... 706/45; 514/12; 435/69.1
(58) Field of Search ........................... 706/45; 711/202; 703/4; 707/532; 345/762; 514/12; 435/69.4

(56) References Cited

U.S. PATENT DOCUMENTS

| | | | | | |
|---|---|---|---|---|---|
| 4,325,120 A | * | 4/1982 | Colley et al. | ............... | 711/202 |
| 4,910,691 A | * | 3/1990 | Skeirik | ......................... | 706/45 |
| 5,339,392 A | * | 8/1994 | Risberg et al. | ............. | 345/762 |
| 5,418,944 A | * | 5/1995 | DiPace et al. | .................. | 707/3 |
| 5,589,452 A | * | 12/1996 | Krstenansky et al. | ......... | 514/12 |
| 5,619,709 A | * | 4/1997 | Caid et al. | .................. | 707/532 |
| 5,693,616 A | * | 12/1997 | Krstenansky et al. | ......... | 514/12 |
| 5,694,523 A | * | 12/1997 | Wical | .......................... | 706/45 |
| 5,695,955 A | * | 12/1997 | Krstenansky et al. | ...... | 435/69.4 |
| 5,798,225 A | * | 8/1998 | Krstenansky et al. | ...... | 435/69.4 |
| 5,807,823 A | * | 9/1998 | Krstenansky et al. | ......... | 514/12 |
| 5,815,415 A | * | 9/1998 | Bentley et al. | ................. | 703/4 |
| 5,840,837 A | * | 11/1998 | Krstenansky et al. | ....... | 630/324 |
| 5,932,445 A | * | 8/1999 | Lal et al. | .................... | 435/69.1 |
| 5,977,070 A | * | 11/1999 | Piazza et al. | .................. | 514/12 |
| 6,010,861 A | * | 1/2000 | Blume | ....................... | 435/7.1 |
| 6,061,675 A | * | 5/2000 | Wical | .......................... | 706/45 |
| 6,140,076 A | * | 10/2000 | Adema et al. | ............. | 435/69.1 |

FOREIGN PATENT DOCUMENTS

WO      WO97 14106 A      4/1997

OTHER PUBLICATIONS

Techniques for Automatically Correcting Words in Text, Karen Kurich, ACM Computing Surveys, vol. 24, No. 4, Dec. 1992.*

Access Methods for Text, Christos Faloutsos, ACM Computing Surveys, vol. 17, No. 1, Mar. 1995, ACM.*

Concurrency+Modularity+Programmability=Mars, Project Start, Vadim E. Kotov, Jun. 1991, Communications of the ACM, vol. 34, No. 6.*

(List continued on next page.)

*Primary Examiner*—Thomas Black
*Assistant Examiner*—Michael B. Holmes
(74) *Attorney, Agent, or Firm*—Frank P. Grassler (57) ABSTRACT

Statistical classification of activities of molecules is a computer implemented methodology of QSAR employing visualization of molecular features and statistical techniques for correlating features of molecules with their observed biological properties. Each molecule is described by noting the presence (1) or absence (0) of a feature of interest. The identification of specific features coded by 1's or 0's is accomplished by recursive partitioning. The data sets are planned or unplanned. The method is also applicable to classification of individuals in biological populations on the basis of their genetic makeup.

73 Claims, 6 Drawing Sheets

OTHER PUBLICATIONS

Fast Text Searching for Regular Expressions or Automaton Searching on Tries, Ricardo A. Baeza–Yates and Gaston H. Gonnet, Journal of ACM, vol. 43, No. 6, Nov. 1996, pp. 915–936.*

ODEXPERT An Expert System to Select Numerical Solvers for Initial Value ODE Systems, M. S. Kamel, K. S. Ma, W. H. Enright ACM Transactions on Mathematical Software, vol. 19, No. 1, Mar. 1993, pp. 44–62.*

Object–Oriented Design of Preconditioned Iterative Methods in Diffpack, Are Magnus Bruaset Sintef, Hans Petter Langtangen, ACM Transactions on Mathematical Software, vol. 23, No. 1, Mar. 1997, pp. 50–80.*

Generating Automatically Tuned Bitmaps from Outlines, John D. Hobby, Journal of the Association of Computing Machinery, vol. 40, No. 1, Jan. 1993, pp. 48–94.*

Drug Design Using Inductive Logic Programming, Ross D. King, Ashwin Srrinivasan, Stephen Muggleton Cao Feng, Richard A. Lewis, Michael J. E. Sternberg, IEEE, 0–8186–1060–3425/93 (1993).*

Sample Complexity of Model–based Search, Christopher D. Rosin, ACM 1998, 1–58113–057—0/98/7.*

Applications of Inductive Logic Programming, Ivan Bratko and Stephen Muggleton, Advances in Traditional AI, Communications of the ACM, Nov. 1995/vol. 38. No. 11.*

RAPID: Randomized Pharmacophore Identification for Drug Design, P. W. Finn, L. E. Kavraki, J. C. Latombe, R. Motwani, C. Shelton, S. Venkatasubramanian, A. Tao, ACM 1997.*

Using Theoretical Descriptors in Quantitative Structure Activity Relationships, George R. Famini and Leland Y. Wilson, IEEE Engineering in Medicine & Biology Society, 1989, Proceedings of the Annual International Conference of the IEEE, vol. 6, 1989.*

Consentino U, et al, "Correlation Of Geometrical Features Of Muscarinic Antagonists With Activity", Organic Crystal Chemistry: Molecular Design, Structure, Reactivity, and Transformation, $9^{th}$ International Symposium, Poznan–Rydzyna, Poland, Aug. 23–27, 1994, vol. 374, ISSN 0022–2860, Journal of Molecular Structure, Jan. 1, 1996, Elsevier, Netherlands, pp. 53–61.

R. Ashany, "Application Of Sparse Matrix Techniques To Search, Retrieval, Classification and Relationship Analysis In Large Data Base Systems—SPARCOM" Proceedings of the International Conference on Very Large. Fouth International Conference. Sep. 13–15, 1978, West Berlin, Germany, pp. 499–516.

King R D, et al, "Comparison Of Artificial Intelligence Methods For Modeling Pharmaceutical QSARS" Applied Artificial Intelligence, Mar.–Apr. 1995, USA, vol. 9, No. 2, ISSN 0883–9514, pp. 213–233.

* cited by examiner

FIG. 6

STATISTICAL DECONVOLUTING OF MIXTURES

This application is filed pursuant to 35 U.S.C. §371 as a United States National Phase Application of International Application No. PCT/US98/07899 filed Apr. 17, 1998, which claims priority from U.S. Pat. No. 60/044,056 filed Apr. 17, 1997.

BACKGROUND OF THE INVENTION

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

This invention relates generally to computer assisted methods of analyzing chemical or biological activity and specifically to computer assisted methods of determining chemical structure-activity relationships, and determining which species in a mixture from a chemical or biological population can be predicted to have a given biological activity or biological phenotype. This method is particularly useful in the fields of chemistry and genetics.

Combinatorial chemistry and high-throughput screening (HTS) are having a major impact on the way pharmaceutical companies identify new therapeutic lead chemical compounds. Voluminous quantities of data are now being produced routinely from the synthesis and testing of thousands of compounds in a high-throughput biochemical assay. The construction of chemical libraries has, in effect, replaced the painstaking individual synthesis of compounds for biological testing with a strategy for the multiple synthesis of many compounds about a common structural core scaffold. Since there is such a low probability of identifying new lead compounds from screening programs, it is expected that the sheer number of compounds made via a combinatorial approach will provide many more opportunities to find novel leads. However, making and testing thousands of compounds instead of fifty to one hundred per chemist per year has placed a tremendous strain on the logistical and computational infrastructure usually relied upon to store and analyze these datasets. Methods, developed in the last decade, for the statistical analysis of a relatively small number of compounds (less than 100) are not suitable for use on much larger data sets. Consequently, new technologies must be investigated.

Various methods for the storage and retrieval of chemical structure/biological activity data have been devised. Software products are now available from major vendors that address most of the logistical needs of combinatorial chemistry. Little thought, however, has been given to how the data might best be used to guide future synthetic efforts once the biological activity of chemical compounds has been learned. One possible result from the synthesis and testing of large numbers of compounds is a short list of promising new lead compounds for further consideration. Many research programs stop here and immediately revert to traditional synthesis in order to optimize the new leads. On the other hand, others are seeking to continue along a combinatorial path have employed an evolutionary approach to make best use of all the data.

Genetic algorithms have also been used to select new chemical libraries to be made. However, due to the complex and specialized nature of the software used to identify 3D pharmacophores, it is unlikely that these methods will be able to routinely handle the volume of data and/or possible multiple binding modes or sites.

For a number of years, there has been an interest in using artificial intelligence methods to deconvolute, uncover hidden rules from, or otherwise classify chemical datasets. Most have focused on reaction prediction. Others have used neural networks, fuzzy adaptive least squares and the like to analyze structure-activity datasets or predict chemical properties. Most of these methods are generally much too complex for routine structure-activity-relationship (SAR) analysis of large heterogenous data sets.

Recursive partitioning (RP) is a simple, yet powerful, statistical method that seeks to uncover relationships in large data sets. These relationships may involve thresholds, interactions and nonlinearities. Any or all of these factors impede an analysis that is based on assumptions of linearity such as multiple linear regression (or basic QSAR), principal component regression (PCR), or partial least squares (PLS). Various implementations of RP exist but none have been adapted to the specific problem of generating SAR. The present invention features a new computer program, Statistical Classification of Molecules using recursive partitioning (SCAM), to analyze large numbers of binary descriptors (which are concerned only with the presence or absence of a particular feature) and to interactively partition a data set into active classes.

SUMMARY OF THE INVENTION

In brief summary, the invention is a computer-based method of encoding features of mixtures, whether the features be of individual data objects in a mixture or features of mixtures themselves, and of identifying and correlating those individual features to a response characteristic that is a trait of interest of the individual data object or of the mixture. The method is applicable to data objects in those types of data sets that are characterized in being a mixture of data object classes, each data object class containing one or more of the data objects, and wherein multiple data objects present a same trait of interest, but classes of data objects produce the response characteristic that is a trait of interest through different underlying mechanisms. The method comprises the steps of: assembling a set of descriptors and converting said set of descriptors into the form of a bit string such that each descriptor reflects the presence or absence of a potentially useful feature in a data object of interest; examining each data object for presence or absence of each of said descriptors; assembling the results of looking for descriptors into a vector for each data object, noting the presence or absence of each feature in said data object; assembling all vectors thus generated into a matrix; dividing the data in said matrix into two daughter sets on the basis of presence or absence of a given descriptor from said set of descriptors; and iteratively repeating this step until each member of said mixture has been classified into a group. The method is applicable to three broad situations. Firstly, those situations in which data objects are unique, but the data set is a mixture in the sense that the data objects act in different ways, e.g. a population of human patients having different biological genotypes that nonetheless lead to a phenotypically identical clinical disease diagnosis. Secondly, those situations in which the data objects are themselves mixtures, e.g. a mixture of k chemical compounds tested together in a high throughput screen, or a mixture of different structural modes of a compound, and those data objects that show a given activity of interest do so in the same fashion or through the same underlying mechanism of action. And thirdly, those situations in which the data objects are mixtures and the active elements in the mixtures produce the same activity, but are acting through different mechanisms, for example, where k chemical compounds are screened together for activity and two of the compounds bind to a biological receptor, but bind to it in different places or in different conformations. Each of these three types of situations can be addressed whether they are planned or inadvertent mixtures. A planned mixture occurs where the fact of being a mixture is capable of manual control as is the case with carrying out a combinatorial synthesis, or where a high throughput screening is carried out with, for example, 20 compounds test together. An inadvertent mixture is said to be present whenever it is inherent in the situation, for example where there are multiple structural conformations of a chemical compound, or where a data set contains compounds producing the same chemical result but acting by different mechanisms, or where a data set contains compounds producing the same biochemical result, but binding to different receptor sites or places, or where the data set is a human population having the same clinical disease, but the individuals have different genetic types coding for different underlying pathologies.

DETAILED DESCRIPTION OF THE PREFERRED EMBODIMENTS AND BEST MODE OF THE INVENTION

The method of the present invention overcomes previous shortcomings in the chemical and biological arts. In a first preferred embodiment, Structure-activity relationships (SAR's) can be developed from large bodies of data generated as a result of high throughput screening (HTS), or combinatorial or other automated chemical syntheses. Such chemical syntheses outputs data sets composed of large numbers of structurally heterogeneous chemical compounds.

First, a set of descriptors is generated. Descriptors, as that term is used in the present invention, are any type of descriptive notation that, in the context of chemistry, are chemically interpretable, have enough detail that they can capture useful chemical structural features, and are capable of being described in terms of being present or absent in a given chemical compound, which in turn confers the ability to describe them computationally as a bit string. A partial, non-limiting list of descriptors can include: atom pairs, which set forth a spatial-qualitative relationship between any two atoms in a molecule; atom triples, which set forth a spatial-qualitative relationship between any three atoms in a molecule; descriptions of molecular fragments; descriptions of molecular topological torsions; any binary of continuous variables; or any combination of any of theses types of descriptors. In the context of biology, a descriptor can be, most preferably, a genetic marker, such that an individual subject in a population of interest either does or doesn't have the marker or a particular allele of a gene.

For any of the above-listed descriptors, or any non-listed descriptors that otherwise fit the above stated criteria, it can readily be seen that for any single chemical compound under consideration, it can be stated that the compound either has or doesn't have the descriptor. This presence or absence of such a descriptor for a compound can be represented computationally as a bit string, by a series of 1's or 0's, each representing presence or absence, respectively, of a given descriptor for the compound under consideration. Multiple descriptors of a given type are generated, and each chemical compound is compared against each descriptor for the presence or absence of each descriptor in the specified set of descriptors that can occur in a data set. This comparison process yields a bit string of 1's and 0's, as the case may be, that constitute a vector.

The vector's sequence of 1's and 0's will be an identifier of the compound under consideration, defining it in terms of the set of descriptors that occur in the data set.

Two types of descriptors can be exemplified. Atom pairs and atom triples are descriptors generated from the topological (2D) representation of a molecular structure. They are very simple descriptors composed of atoms separated by the minimal topological distance (i.e., the number of bonds) between them, or equivalently, the number of atoms in the shortest path connecting the atoms. Each local atomic environment is characterized by three values: the atomic number, the number of non-hydrogen connections and one-half of all associated π-electrons. For example, the carbonyl carbon in acetone is encoded as [C, 3, 1] whilst a terminal methyl carbon would be [C, 1, 0]. The code for the carbonyl oxygen is [O, 1, 1, 1]. Thus, for each structure, (n (n-1))/2 atom pairs (where n is the number of non-hydrogen atoms in a structure) are generated by considering each atom and the minimal topological distance to every other atom in turn. A bit-string indicating the presence or absence of a particular atom pair was then produced. In general, approximately ten thousand unique types of atom pairs are generated for a typical data set of about one thousand structures.

The second type of structural descriptor, atom triangles, or atom triples, have been used by several groups for molecular similarity searching and as search keys for 3D search and docking studies. Triangles of atoms with corresponding interatomic distance information are thought to be the most elemental portions of a pharmacophore. Our atom triangles differ from those previously defined. As an indication of interatomic distance, we consider only the length of the shortest path between each pair of atoms forming the triangle. For example, the triangle formed amongst the carbonyl oxygen and the two terminal methyls of acetone is [O, 1, 1] (2); [C, 1, 0] (2); and [C, 1, 0] (2). All possible triangles are generated and each is properly canonicalized to a unique form and then transformed into a bit string as with atom pairs. Often, depending upon the diversity and size of the data set, it is possible to generate hundreds of thousands to millions of unique atom triples. For a 90,000 compound data set there are on the order of over 2 million possible atom triples.

Figure 4:
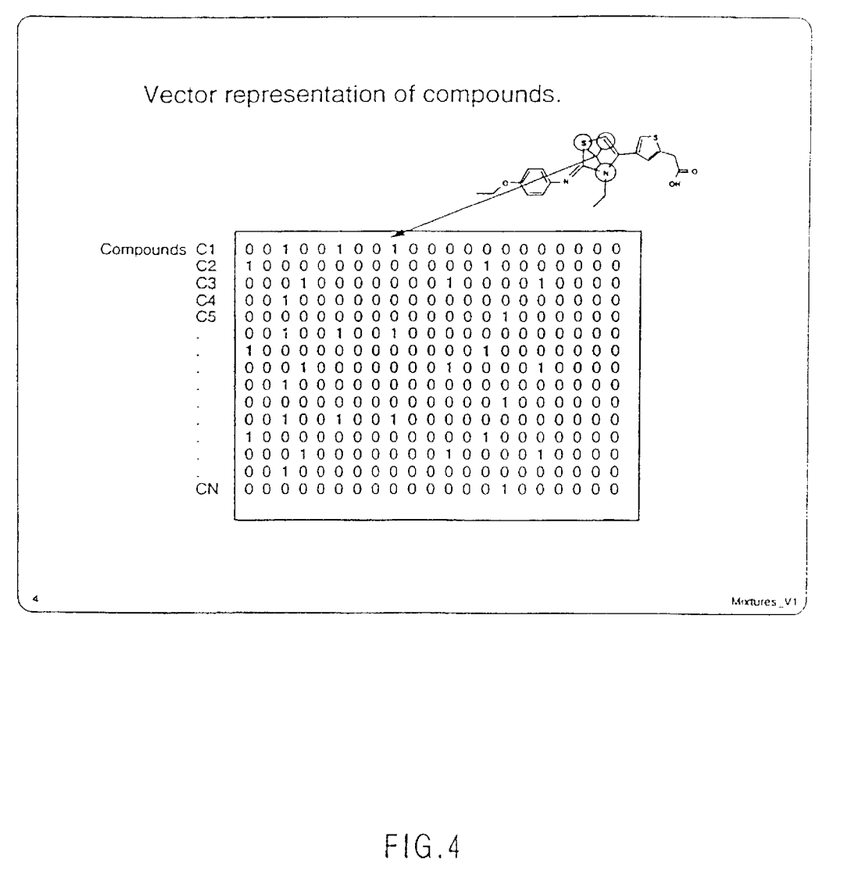
FIG. 4 is an illustration of a matrix having multiple vectors representing compounds.

A bit string is built computationally as long as the number of distinct features, e.g., atom triples, in an initially specified data set. The bit string is initially populated with 0's. Any given 0 is changed to a 1 if a compound being examined has at least one atom triple of the type assigned for that position in the bit string. As multiple compounds are thus examined, a matrix of the type shown in FIG. 4 is created, consisting of 1's and 0's. Such a matrix can grow to extremely large size, with over 2,000,000 descriptors not being uncommon. However, since most of the positions will be 0's, denoting the absence of a descriptor for that compound, this means the matrix is sparse. A sparse matrix is computationally handled in the present invention by only keeping track of where the 1's are, and imputing the positions of the 0's, thus compressing the bit string and saving an enormous amount of computer memory. The bit string is subsequently decompressed when necessary.

In the meantime, an empirically obtained database of the potency (for some chemical or pharmacological reaction of interest) of each of the compounds or mixtures being examined has been assembled. Taking the data consisting of the assembled 1's and 0's in the matrix and the known potency for each compound, the task is to divide the data into two groups, with data objects with 1's assigned to one group and data objects with 0's assigned to the other, thus effectively splitting the data into less active and more active compounds.

The best column to use to divide the data set must be found. This optimal column is found through the use of the tool known as recursive partitioning (RP). RP analysis generates a diagram as exemplified in FIG. 5. In the diagram in FIG. 5, the node at the top of the tree is designated as Node 0. It represents a population or set of 1650 compounds, some of which are active, but many of which are inactive, whose potency was previously determined (active compounds are assigned a score of 1, 2 or 3, while inactive compounds are assigned a score of 0), and as a group is now said to have an average potency of 0.34. In general, the number of screened compounds needed to build a analysis tree of this type is at least 100 or more, with 200 or more being preferred and 1,000 or more being most preferred. Immediately under Node 0 is a description of an atom triple, C(1,2)-8-; C(2,1)-6-; and C(1,0)-5-. The RP algorithm examines the difference in potency between groups where each triple (or any other descriptor) is present or absent. The RP algorithm has identified this triple as being the best atom triple to partition off active compounds from inactive compounds in the group of 1650, since this triple results in the largest possible difference in average potency between all possible presence/absence pairs, the difference with the smallest p-value using a statistical test. The algorithm has here split off 37 compounds having this triple, and 37 is the number that appears in the next lower node to the right of Node 0 (all compounds not having this triple are split off to the left). These 37 compounds have an average potency of 2.8, out of a maximum possible of 3. Thus, the algorithm has already identified an atom triple that is a chemical structure feature tending to confer a high degree of chemical reactivity on this class of compounds, and a structure-activity relationship begins to emerge. The RP algorithm next identifies the atom triple C(1,2)-4-;N(3,0)-2-;C(2,0)-3- as being the next best atom triple to partition off active compounds from inactive compounds in the remaining group of 37. This round of partitioning results in two compounds lacking the triple being split off to the left, and the remaining compound being split off to the right. The two compounds split off to the left have no activity, while the other 35 compounds have an average activity of 2.94 out of a possible 3, as stated in the lowermost right side node, call a terminal node). Now a structure-activity relationship is seen in which the presence of the two defined triples reflects a high degree of average potency in the compound subgroup. A typical molecular structure bearing these two atom triples is given, and it can be said with relative confidence that molecules having this general structural core will be active in the screen of interest here (atoms marked with circles are those that belong to the defining atom triples for that node).

Figure 5:
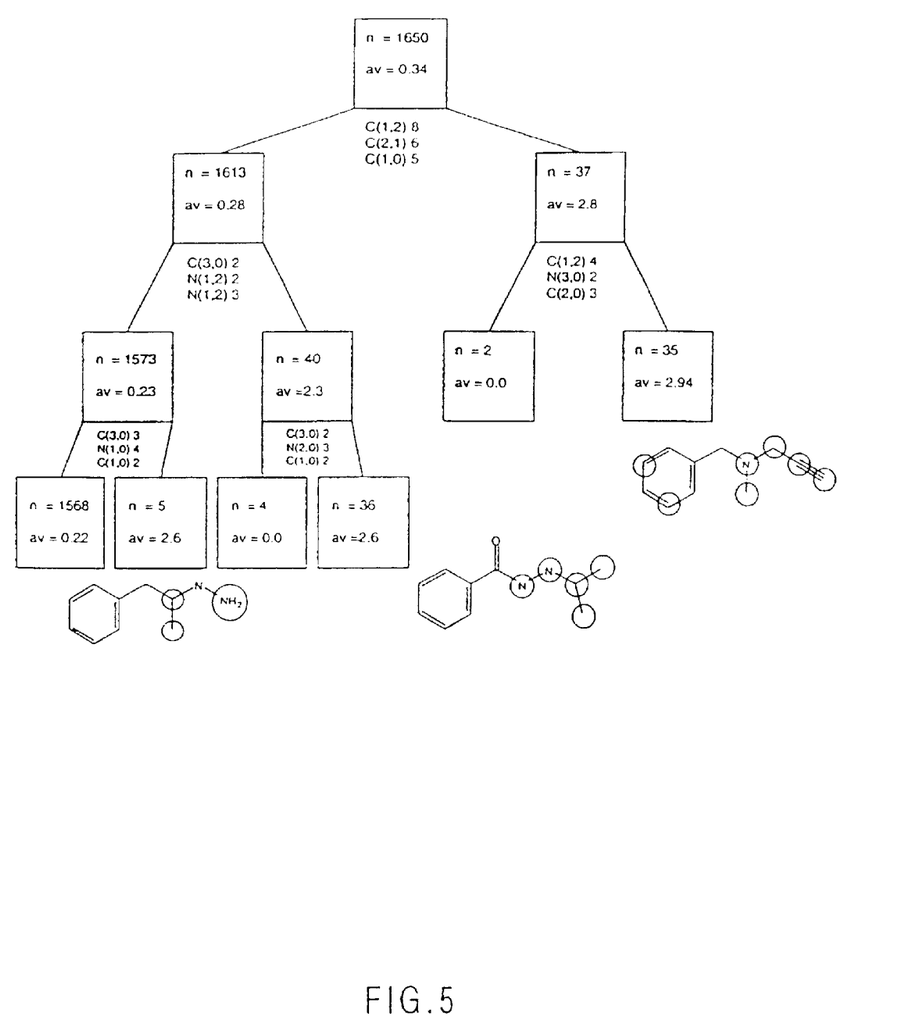
FIG. 5 is an illustration of an analysis tree (also known as a Pachinko tree) generated using recursive partitioning as part of the invention in order to classify structural features of a group of chemical compounds.

However, it can be seen that two other good terminal nodes showed up in this analysis, resulting in three chemical structureclasses being generated in FIG. 5. When the first round of partitioning took place, the algorithm took the remainder of 1613 compounds and identified an atom triple tending to confer activity within that group, C(3,0)-2-;N(1, 2)-2-;N(1,2)-3-, and partitioned that subgroup accordingly into two subgroups having average potencies of 2.3 and 0.23, reflecting the presence or absence of that atom triple. The partitioning process continues until terminal nodes were reached, yielding three structure-activity relationships. These three structural cores can be seen to have somewhat different chemistries. Thus, the original activity of the group of 1650 may be the result of different biochemical/chemical mechanisms. RP can deal with such mixtures of compounds that follow different mechanistic paths.

Having developed such a tree, it is then possible to predict the activities of compounds that have not yet been empirically tested for activity. A given compound is analyzed for presence or absence of triples, or whatever the descriptor is that has been chosen, and then cascaded down the tree with the help of a software tool that is part of the present invention, which is designated as Pachinko. Having examined the compound for the presence or absence of those descriptors now known to confer activity, the activity of the compound is electronically predicted, eliminating the need for high throughput screening of large numbers of compounds which will not have a desired threshold of activity. Those compounds having the greatest predicted activity are selectively tested, at great cost and time savings.

It is important to understand that not only discrete compounds or individuals can be assigned to passed through nodes in the analysis tree, but mixtures themselves as well. Thus, a situation in which 1,000 pools each containing 10 different compounds, isomers, conformers, etc., can be analyzed, in which each pool is now defined and analyzed in terms of descriptors present in the pools. Broadly speaking, discrete compounds or individuals are data objects (an object that itself is not a mixture), but such pools are themselves also each a data object, which we refer to as a mixture object for greater clarity (i.e. an object that is itself a mixture). Whether an object is a data object or a mixture object, the object is analyzed in the same fashion using bit string assembly and recursive partitioning.

Situations commonly arise in which multiple binding modes exist by which several given compounds may be showing the same biological potency, but are doing so by binding to different available binding sites on a receptor molecule, a common situation in pharmacology. A related problem is that of a cell that presents more than one receptor site such that structurally differing molecules can elicit the same biological response from the cell. These problems are increased by orders of magnitude when combinatorial testing is carried out. The problem here is in figuring out what different structural features out of such a mix can confer activity and applying that knowledge to the design or screening of new compounds. The present invention can resolve such mixture problems by assembling a set of descriptors that can define a population of compounds and then proceeding with the rest of the analysis as described to arrive at structure-activity relationship rules out of the mixture.

Yet another problem that can be addressed by the present invention is that in which pairs of compounds may acting synergistically to elicit a chemical or pharmacological response, and where a plurality of pairs is present in a pool to be analyzed. The method of the present invention can be used to find such pairs in a pool and quantify their relative activity as synergistic pairs. As set forth above, not only discrete compounds can be analyzed as data objects but also mixtures as mixture objects. Thus, where no individual compounds (objects) decode into a node, but one or more pairs of compounds (mixture objects) decode into the same node that shows a high average potency, then this result implies the discovery of a synergistic pair of compounds, with members of the the pair having the characteristics of the descriptors leading to that node. Synergistic triples, etc., of compounds can be found in like manner.

Figure 6:
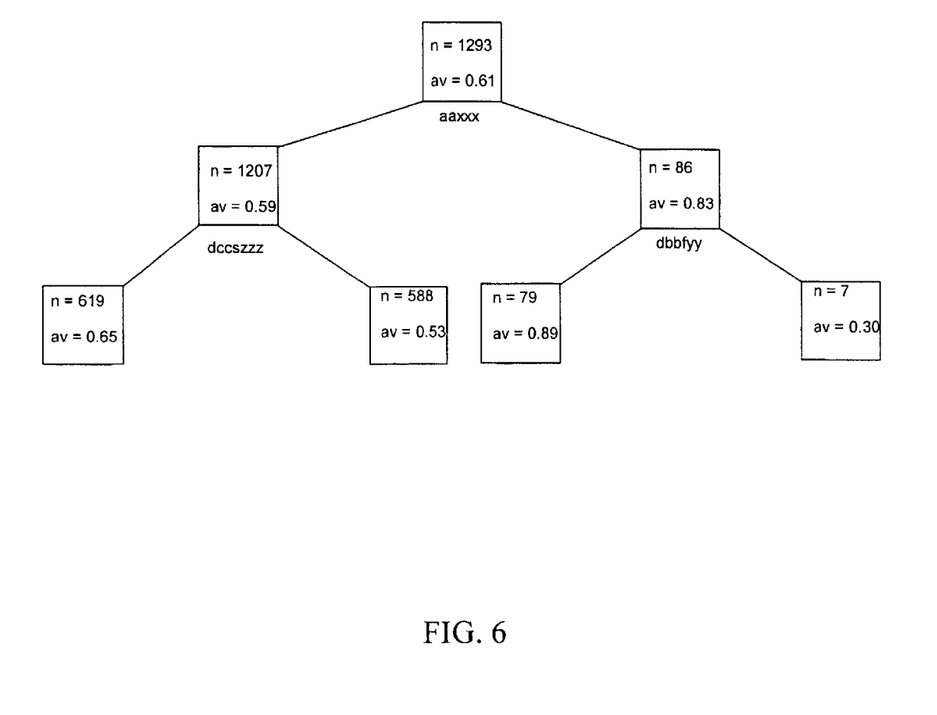
FIG. 6 is an illustration of an analysis tree generated using recursive partitioning as part of the invention in order to classify genetic features of a population.

In genetics, it is common for a population to have individuals in it that are different genotypes. It is now known that a great many diseases are controlled by not one, but multiple genes in an individual. These two factors present a huge problem in unraveling how to rationally target a drug therapy at a population of patients who may have the same clinical diagnosis, but whose pathology is being controlled by multiple possibly different genes within each patient. Until now, there has been no known satisfactory method for the identification of multiple interacting genes from large genomic data sets. However, the present invention addresses this by using alleles or combinations of alleles and/or gene markers as descriptors. Thus, as shown in FIG. 6, a patient population of 1293 individuals had an average disease incidence of 0.61. The RP algorithm selects the gene marker aaxxx, present with two copies, to do a partition. This results in a subgroup of 86 individuals being split off to the right, 83% of whom had disease, while a subgroup of 1,207 not having that genetic marker is split off to the left, and having a disease incidence of 59%. The analysis is continued until terminal nodes are reached that lead to the prediction that the highest incidence of disease will occur in those individuals having two copies of the aaxxx gene but who do not have the gene dbbfyy, which thus appears to be linked to a protector gene that tends to confer protection from disease on an individual, since those that had the putative protector gene only had a 30% incidence of disease. Using these results, after obtaining a genetic analysis of an individual's DNA, their chances of becoming a disease victim can be predicted, and their therapy can be tailored accordingly if the drug being used is one which acts upon a protein expression product of one or more of the genes markers used as descriptors or a near by gene.

Since the economics of high throughput screening favor screening mixtures of compounds, the questions then arise of how to analyze such pooled data, and how to pool them. In another preferred embodiment of the invention, RP can be used to analyze such pooled data.

Discrete products of a combinatorial synthesis can be encoded and decoded by use of the present invention, since each vector as described above is an identifier of the features of a compound. A given compound from a combinatorial synthesis (especially a virtual synthesis, see U.S. Pat. No. 5,463,564) is electronically dropped down an analysis tree and if it lands in a given terminal node showing high activity, it is now known to have both a high probability of activity by virtue of all descriptors assigned to each node through which it passed successfully. This eliminates screening and identification of the great majority of compounds in a virtual combinatorial library, as it is well known that the great majority of combinatorial discrete are chemical 'junk' that will not have any appreciable biological activity, but still have to be winnowed out of a combinatorial pool, currently at great wasted expense.

SCAM was the software tool developed as part of the present invention to perform recursive partitioning by swiftly computing binary splits on a large number of descriptor variables. There are several aspects of implementation to consider. Huge sparse matrices, tens of thousands of structures and millions of descriptors have to be handled, efficient binary splits on up to a million or more variables have to be routinely performed, and a useful bridge for the chemist between the statistical analysis and the actual structures have to be devised.

Three files are produced prior to a SCAM analysis: (1) a data file containing the compound names and potencies; (2) a descriptor dictionary file containing a contextual decoding of each descriptor variable; and (3) a binary file containing a record for each structure that lists all computed descriptors. To conserve memory, a sparse storage format is employed that correlates each descriptor with a list of the structures in which the descriptor is found is stored. This is. very similar to the concept of indirect keys used in substructure search. An alternative is to store a list of descriptors that are found in each structure. However, the former is more efficient, since the t-test is performed on the activities of the structures associated with a particular descriptor.

In contrast to data partitioning via continuous descriptor variables, binary classification trees can be computed very quickly and efficiently since there are far fewer and much simpler computations involved. For example, FIRM develops rules for splitting based on "binning" of continuous variables and amalgamating contiguous groups of variables. These processes add considerably to execution time and effectively limit the interactive nature of most general RP packages for large data sets. However, with binary data a parent node can only be split into two and only two daughter nodes. Splitting on a binary descriptor such as the presence or absence of an atom pair involves performing a t-test between the mean of the group that has the atom pair and the group that does not. The t-values for each rule as a potential split can then be compared using the largest t-statistic. The atom pair with the largest t-statistic is the splitting variable. Therefore, the p-value (a time-consuming part of the calculation) needs only to be computed for the most significant split. Adding to the speed is the fact that, frequently, either the group that has the atom pair or the group that does not have the atom pair is usually quite small. This fact can be exploited using an idea known as "updating" which can be applied to a well known expression for computing the sample variance.

If one denotes the potencies in group 1 by $x1, x2, \ldots, xm$ and group 2 by $y1, y2, \ldots, yn$ and assuming that group 1 is smaller than group 2 (m<n), the t-statistic for testing for a difference between group potency means is:

$$T = \frac{\bar{x} - \bar{y}}{\sqrt{\frac{1}{m} + \frac{1}{n}} \sqrt{\frac{SSX + SSY}{n + m - 2}}}, \text{ where}$$

$$SSX = \sum_{i=1}^{m}(x_i - \bar{x})^2, \quad \bar{x} = SX/m, \quad SX = \sum_{i=1}^{m} x_i$$

$$SSY = \sum_{i=1}^{n}(y_i - \bar{y})^2, \quad \bar{y} = SY/n, \quad SY = \sum_{i=1}^{n} y_i$$

Next, let z1,z2, . . . ,zm+n, denote the potencies in the parent node. The sum, SZ, was computed for the previous split so it is available. Therefore, after computing SX, SY can be computed as the difference SY=SZ−SX. This technique is known as "updating".

A similar updating method can be used to compute SSX and SSY. Note that:

$$SSX = \sum_{i=1}^{m} x_i^2 - \bar{x}^2$$

$$SSY = \sum_{i=1}^{n} y_i^2 - \bar{y}^2$$

so SSY can be computed using the sum of the data, SY, and the sum of the squared data which will be denoted by SYY. Having computed SXX, and having SZZ available, SYY can be computed by the relation SYY=SZZ−SXX. Therefore, the t-statistic can be computed very quickly, having stored the sum of the data and the sum of the squared data from the previous split.

The partitioning is repeated until a stop criteria is met. Firstly, the process can stop if there is no statistical test (t-test is preferred) that achieves a specified level of statistical significance. Secondly, the process can stop if the mixtures in a node are homogeneous with respect to their measured property. Thirdly, the process can stop if the size of each terminal node is below a user specified value.

Example Analysis

Use of RP to uncover substructural rules that govern the biological activity of a set of 1,650 monoamine oxidase inhibitors (MAOI's).

A series of 1,650 MAOI's was used to illustrate the effectiveness of SCAM in analyzing large structure-activity datasets and producing SAR rules. Neuronal monoamine oxidase [amine:oxygen oxidoreductase(deaminating) E.C. 1.4.3.4] inactivates neurotransmitters such as norepinephrine by converting the amino group to an aldehyde. Inhibitors of this enzyme are thought to be useful in the treatment of depression and were introduced into therapy in 1957 with the drug pargyline. However, due to toxicity concerns and interactions with other drugs and food, they are now only occasionally used. Yet, there is continued interest by pharmaceutical researchers of MAO as a target for rational drug design in anti-depressant therapy. Biological activities were reported in four classes of MAOI's: 0 being inactive; 1, somewhat active; 2, modestly active and 3, being most active. Generating any type of QSAR from this dataset would previously have been considered by those of skill in the art to be relatively quite difficult, but use of the present invention in statistically determining SAR rules is now possible and relatively easy.

Figure 1:
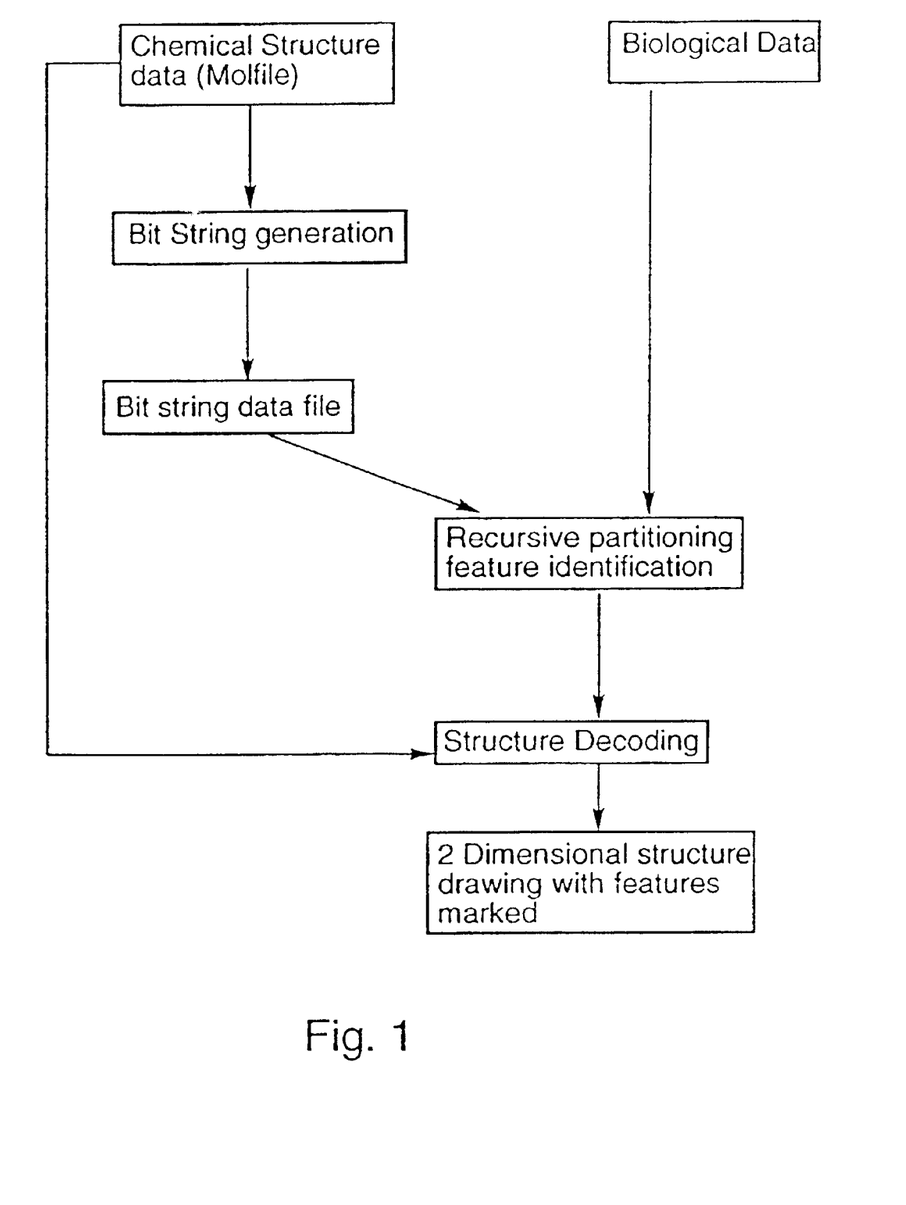
FIG. 1 is a schematic illustration of the process to identify important features of individual compounds in a mixture.
Figure 2:
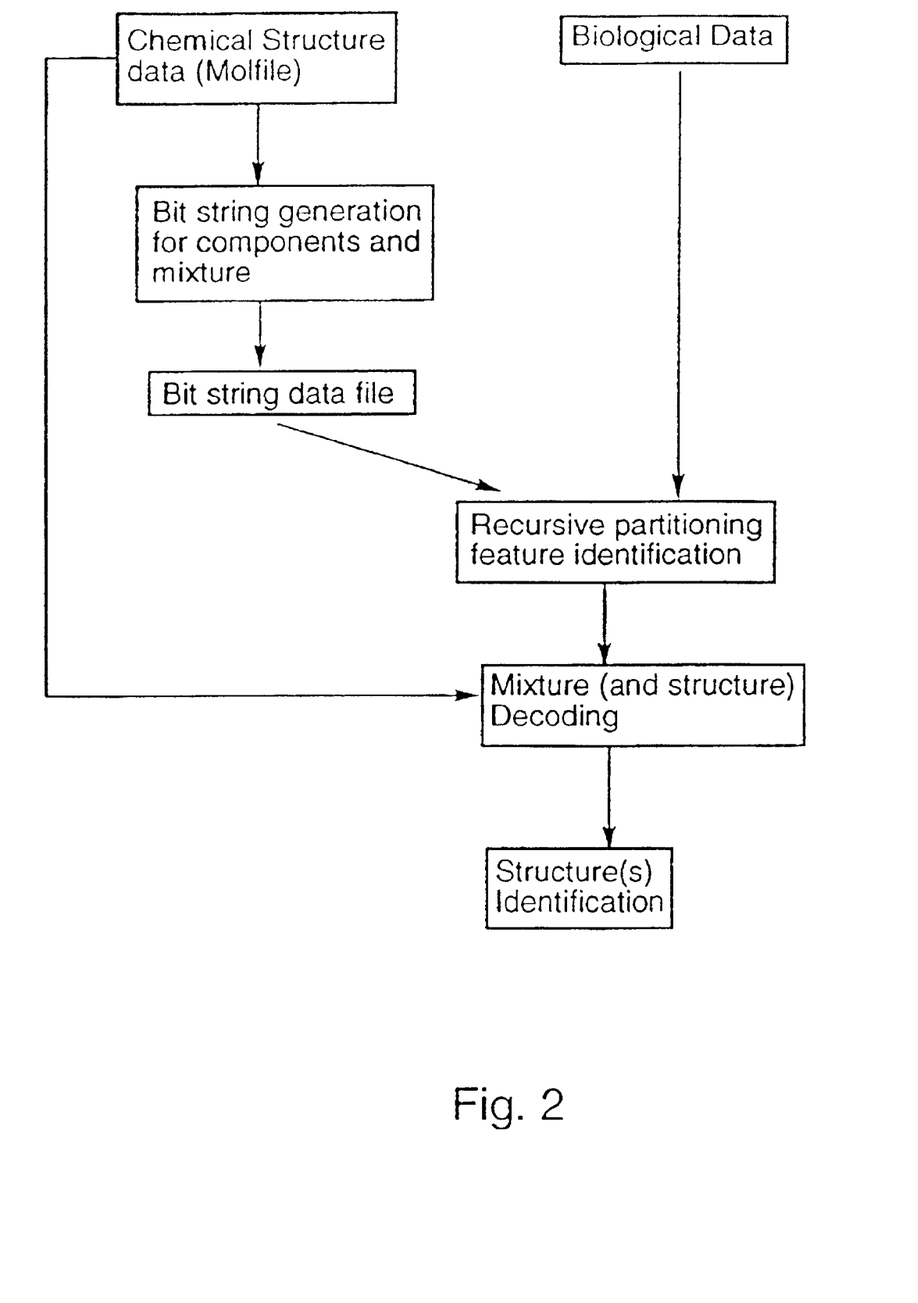
FIG. 2 is a schematic illustration of the process to identify important features of a mixture and identify active components.
Figure 3:
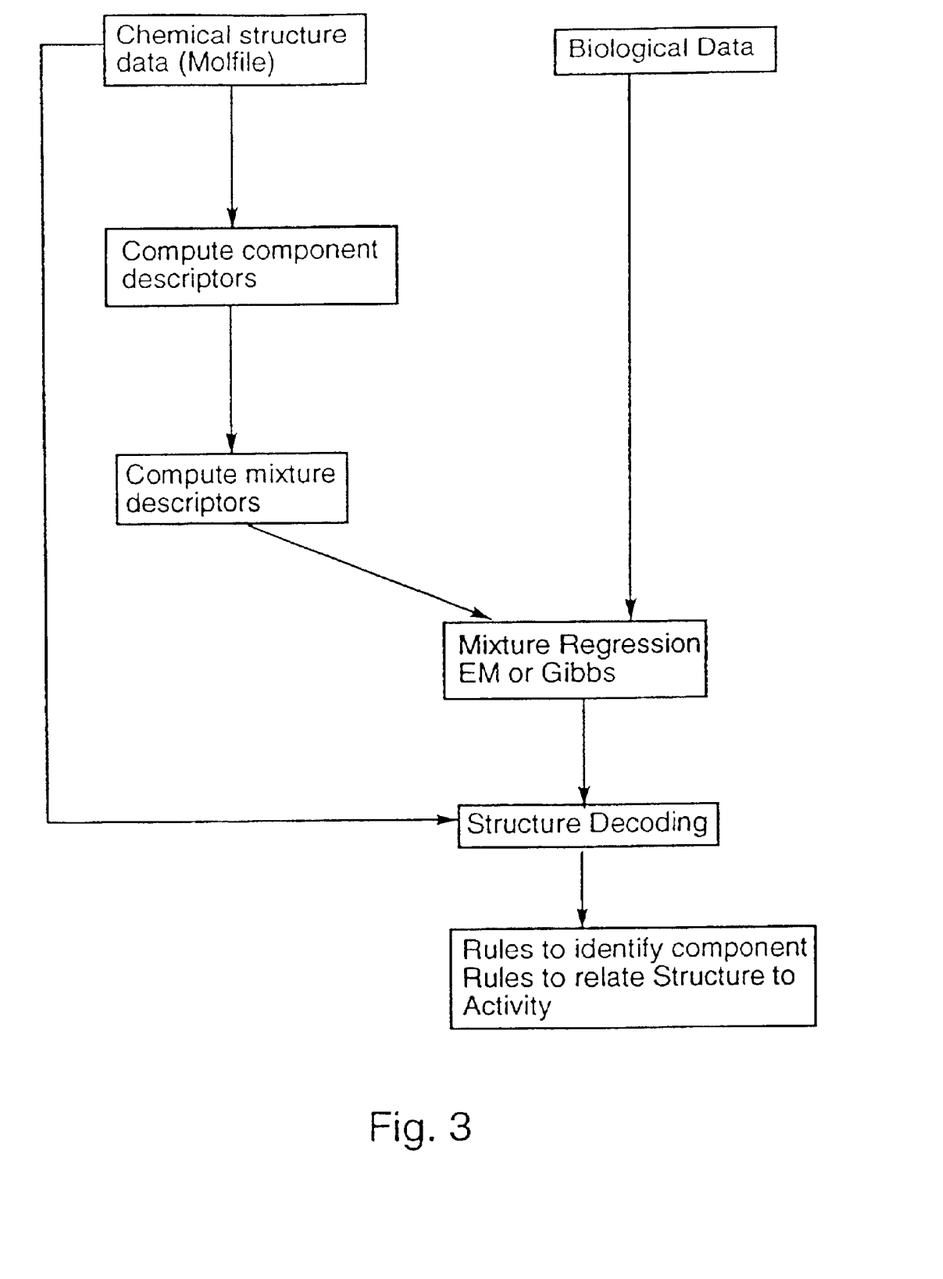
FIG. 3 is a schematic illustration of the process to identify active component(s) of a mixture and the features associated with biological activity of chemical structures.

Recursive partitioning was applied to this set of 1,650 activities and unique atom pairs and the resulting tree diagram is shown in FIG. 1. Default settings were used to produce this tree: up to 10 levels of partitioning are allowed, each split is statistically significant (Bonferroni adjusted p-value <0.01), and both positive and negative splits were allowed. The Bonferroni p-value is computed by multiplying the raw p-value by the number of variables examined at the node. Eleven significant splits were found although a high percentage, 79.5% (70/88), of the most active molecules are found in only 3 terminal nodes (shaded in gray).

To facilitate the understanding of the splits of the data obtained from recursive partitioning, it was necessary to have a molecular viewer which could not only display molecules, but highlight the portions of the molecules described in the rules. SCAM is not locked into displaying only one type of descriptor, but rather passes the descriptor variables path to a node to an external program which highlights the appropriate atoms or bonds and then passes the structure along to a viewer. To SCAM, descriptors are just strings, and it is up to external programs to interpret the results and display them. The external programs can be specified by simply specifying external environment variables.

SCAM has an option that allows the user to enter a MDL SD-file containing the structures for the compounds. Rather than reading them directly into memory, as the files can be quite huge, a list of seek indices is computed once on the SD-file. Then, whenever the user requests to see the compounds at a node, it is a simple matter of performing seeks to the appropriate offsets in the SD file to obtain the compounds of interest.

When examining the RP classification tree, it is often of great interest to see the distribution of potencies at a node and to see how a split at a node divides up the potencies at the two daughter nodes. A non-parametric density plot is available to display the potency distribution at the node, with the potency distribution of the two daughter nodes overlaid in different colors The density plot is performed by weighting each point by a Gaussian kernel function with a configurable bandwidth. If the assay variability is known, then the assay standard deviation can be used for the bandwidth.

AT Tree

Once the analysis has been completed, a file describing the rules that create an RP tree can be written to disk, and a utility program, Pachinko, can be invoked on a new dataset to find where the compounds in that dataset would fall in the classification tree. Thus, a set of compounds can be screened, analyzed with SCAM producing a classification tree, and then a whole corporate chemical compound collection, or even virtual chemical compound libraries can be dropped down the tree to suggest additional compounds for biological screening. With Pachinko it is also possible to divide data into training and validation datasets to test the predictive powers of the tree.

With a large number of descriptor variables, it is often the case that there is more than one descriptor that would give rise to the same split at a node. These variables are considered to be perfectly correlated. When the variable associated with the most significant split has other perfectly correlated variables, all such descriptors at the node are stored so that these rules can later be used for as input to the Pachinko program. In the dataset used to create the tree, all correlated variables will be found within the structures at a right node, though, in theory, only one would be necessary in order for some novel structure to be placed there. Within the Pachinko program, there is an option to either force all correlated variables to match for a rule to be satisfied, or else to have any one matching descriptor for the right path in a tree to be taken.

There is now set forth a pseudocode example for carrying out the SCAM function. SCAM is implemented in C code using the XVT Development Solution for C, a tool for building Graphical User Interfaces in C. SCAM is menu-driven.

1. File Menu

File commands are used to import the data files associated with SCAM, enter documentation, and send print output to a file.
1.1 Import
   read the .dat file and store compound names and potencies in arrays;
   read the .des file and store descriptor codes and names in arrays;
   read the .bit file and create a matrix which has a row for each descriptor and,
      in each row, an array of indices (into the compounds array) of all compounds that have that descriptor;
1.2 Read Structures
   calculate a set of seek indices into an SD file so that molecular structure information can be accessed quickly;
1.3 Edit Information Box
   allow the user to input information about the data set being analyzed;
1.4 Print Tree
   write the current tree to a postscript file for later printing;
1.5 Quit
   quit SCAM;

2 Menu Tree

Most of the options in the tree menu operate on the currently active node, which the user indicates by positioning cursor over a node and clicking the left mouse button.
2.1 Split Node
   split the active node into two children nodes using the descriptor which provides the most statistically significant split;
   bonferroni:=number of descriptors;
   t:=0; /*holds the t-statistic for the best split*/
   every descriptor in the data set do

```
{
   split the compounds in the active node into two groups
   according to whether or not they have the descriptor;
   if the descriptor appears in no or all compounds then
      bonferroni: = bonferroni -1;
   else
   {
      calculate the t-statistic for this split:
         t =
      where:
      χ = mean potency of compounds in left or right child
      σ = standard deviation of compound potencies of
      node being split
      η = number of compounds in left or right child
      if    /*largest t-statistic indicates the most significant split *
         tbest: = t
   }
}
``` compute the pvalue from tbest and multiply this by the bonferonni adjustment to get a value indicating the significance of the split;

2.2 Delete Subtree
   delete the subtree rooted at the currently active node;
2.3 Split Subtree Recursively
   while (tree depth from active node<maximum-depth AND further splits can be found) do
      split a terminal node of the tree rooted at the currently active node
2.4 View Structures
   filter an SD file containing the compounds in the active node through an external progra which highlights the atoms in the compounds that correspond to the descriptor variables (including correlated ones) that got the compound to that node;
   send the filtered SD file to a viewer program (Project View);
2.5 Structures→Clipboard
   copy the structures at the active node to the clipboard in the form of an SD file;
2.6 Save Structures
   write all structures (with atom highlighting-see Section 2.4) within the active node to an file;
2.7 List Node
   write a list of the compounds and potencies within the active node to an external file;
2.8 Node Potency Histogram
   draw a non-parametric density plot of the potencies of the active node;
2.9 Write Pachinko Subtree Rules
   write the rules that generated the tree rooted at the active node to an external file;
2.10 Create .dat File for Node create a .dat file for the compounds in the active node;
2.11 Options
   review and/or alter the options (split method, minimum split size, split significance, maximum tree depth, potency thresholds for highlighting) that determine how nodes are split and how the tree is displayed;
   Copyright 1997 by Glaxo Wellcome, Inc., all rights reserved, except as stated above.

There is now set forth a pseudocode example for carrying out the function of prediction of activity of a molecule by Pachinko if rules from SCAM/Recursive Partitioning have been previously stored.
   For each rule used to split data;
      input Node Tree Position;
      input Node Average;
      input Node Number Rules;
      input Node Rule Set:
   For each object to be predicted
   Current Tree Position:="N";
   Object Activity:=Node Average at Current Tree Position;
   Input Object Name;
   Input Object Rule Set;
   While Node Number Rules at Current Tree Position is greater than 0
      for every rule $r_i$, in Node Rule Set at Current Tree Position
         if $r_i$ is not an element of ObjectRule Set at Current Tree Position
            Current Tree Position :=Current Tree Position+ "0";
         next Rule Set;
   Current Tree Position :=CurrentTree Position="1";
   Object Activity:=Node Average at Current Tree Position;
   print Object Name, Object Activity;

Copyright 1997, 1998 by Glaxo Wellcome, Inc., all rights reserved except as stated above

What is claimed is:

1. A computer-based method of encoding features of data objects, and of identifying and correlating individual said features to a response characteristic that is a trait of interest of the data object, applicable to data objects in a data set that is characterized in being a mixture of data object classes, each data object class containing one or more of said data objects, and wherein multiple data objects present a same or similar value of the trait of interest, but classes of data objects produce the response characteristic that is a trait of interest through different underlying mechanisms, comprising the steps of:
  (a) assembling a set of descriptors and converting said set of descriptors into the form of a bit string such that each descriptor reflects the presence or absence of any given potentially useful feature of interest in a data object of interest;
  (b) examining each data object for presence or absence of each of said descriptors;
  (c) assembling the results of step (b) into a vector for each data object, noting the presence or absence of each feature of interest in said data object;
  (d) assembling all vectors generated in step (c) into a matrix with each row of the matrix corresponding to a data object and each column corresponding to a feature of interest;
  (e) dividing the data in said matrix into two daughter sets on the basis of presence or absence of a given feature of interest from said set of descriptors; and
  (f) repeating step (e) until each member of said matrix has been identified in terms of presence or absence of any given feature of interest from said set of descriptors and each of said members has been assigned to a terminal node.

2. A computer-based apparatus system for allowing a user thereof to encode features of data objects, and to identify and correlate individual said features to a response characteristic that is a trait of interest of the data object, applicable to data objects in a data set that is characterized in being a mixture of data object classes, each data object class containing one or more of said data objects, and wherein multiple data objects present a same or similar trait of interest, but classes of data objects produce the response characteristic that is a trait of interest through different underlying mechanisms, comprising:
  (a) input means responsive to operator commands enabling an operator to specify a set of descriptors that are subsequently converted into a bit-string, such that each descriptor reflects the presence or absence of a potentially useful feature of interest in a data object of interest;
  (b) storage means for storing the assembled set of (a);
  (c) memory means for executing programmed steps that examine each data object for presence or absence of each of said descriptors;
  (d) means for assembling the results of (c) into a virtual matrix with each row of the matrix corresponding to an object and each column corresponding to a feature of interest;
  (e) means for assigning each data object in said matrix recursively into one of two defined categories on the basis of presence or absence of a given feature of interest from said set of descriptors and repeating such analysis until each member of said mixture has been identified in terms of presence or absence of features of interest from said set of descriptors and assigned to a terminal node; and
  (f) output means for visually displaying, using computer graphics, a relationship of said descriptors with said data objects and classes.

3. A computer software system having a set of instructions for controlling a general purpose digital computer in performing a desired function comprising:
  a set of instructions formed into each of a plurality of modules, each module comprising:
    (a) an input process responsive to operator commands enabling an operator to specify a set of descriptors and convert said descriptors into a bit string such that each descriptor reflects the presence or absence of a potentially useful feature of interest of a data object of interest, wherein each data object is a member of a data set that is characterized in being a mixture of data object classes, each data object class containing one or more of said data objects, and wherein multiple data objects present a same or similar trait of interest, but classes of data objects produce the response characteristic that is a trait of interest through different underlying mechanisms;
    (b) a data storage process for storing the assembled set of (a);
    (c) a computational process for executing programmed steps that examine each member of said mixture for presence or absence of each of said descriptors;
    (d) a computational process for assembling the results of (c) into a vector for each data object and a matrix for all vectors;
    (e) a computational process for assigning each data object in said matrix into one of two defined categories on the basis of presence or absence of a given feature of interest from said set of descriptors and repeating such analysis until each member of said mixture has been identified in terms of presence or absence of each feature of interest from said set of descriptors and assigned to a terminal node;
    (f) a data storage process; and
    (g) an output process for visually displaying, using computer graphics, a relationship of said descriptors with said data objects and classes.

4. A computer-based method of encoding mixture features of planned mixtures or of inadvertent mixtures, or of a combination of planned or inadvertent mixtures, and of identifying and correlating individual said features to a response characteristic of the mixture object, wherein said mixture object is in a data set wherein multiple mixture objects comprising the data set present the same trait of interest through a common underlying mechanism;

comprising the steps of:
  (a) assembling a set of descriptors and converting said set of descriptors into the form of a bit string such that each descriptor reflects the presence or absence of a potentially useful feature of interest in a mixture object;
  (b) examining each mixture object for presence or absence of each of said descriptors;
  (c) assembling the results of step (b) into a vector for each mixture object, noting the presence or absence of each feature of interest in said mixture object;
  (d) assembling all vectors generated in step (c) into a matrix with each row corresponding to a mixture object and each column corresponding to a feature of interest;

(e) dividing the mixture objects in said matrix into two defined daughter nodes on the basis of presence or absence of a given feature of interest from said set of descriptors; and (f) repeating step (e) until each mixture object of said matrix has been identified in terms of presence or absence of given features of interest from said set of descriptors and assigned to a terminal node.

5. A computer-based apparatus system for allowing a user thereof to encode features of planned mixtures or of inadvertent mixtures, or of a combination of planned or inadvertent mixtures, and to identify and correlate individual said features to a response characteristic of the mixture object, wherein said mixture object is in a data set wherein multiple mixture objects comprising the data set present the same trait of interest through a common underlying mechanism, comprising:

(a) input means responsive to operator commands enabling an operator to specify a set of descriptors that are subsequently converted into a bit string, such that each descriptor reflects the presence or absence of a potentially useful feature of interest in a mixture object of interest;

(b) storage means for storing the assembled set of (a);

(c) memory means for executing programmed steps that examine each mixture object for presence or absence of each of said descriptors;

(d) means for assembling the results of (c) into a virtual matrix with each row corresponding to a mixture object and each column corresponding to a feature;

(e) means for assigning each mixture object in said matrix recursively into one of two defined categories on the basis of presence or absence of a given feature of interest from said set of descriptors and repeating such analysis until each mixture object of said matrix population has been classified in terms of presence or absence of given features of interest from said set of descriptors and assigned to a terminal node; and (f) output means for visually displaying, using computer graphics, the relationships of said descriptors with said mixture classes and mixture objects.

6. A computer software system having a set of instructions for controlling a general purpose digital computer in performing a desired function comprising:

a set of instructions formed into each of a plurality of modules, each module comprising:

(a) an input process responsive to operator commands enabling an operator to specify a set of descriptors and convert said descriptors into a bit string such that each descriptor reflects the presence or absence of a potentially useful feature of interest in a mixture object of interest, wherein each mixture object is a member of a data set where each mixture object presents a same trait of interest through a common underlying mechanism;

(b) a data storage process for storing the assembled set of (a);

(c) a computational process for executing programmed steps that examine each member object of said data set for presence or absence of each of said descriptors;

(d) a computational process for assembling the results of (c) into a vector for each mixture object and a virtual matrix with each row corresponding to a mixture object and each column corresponding to a feature;

(e) a computational process for analyzing the data in said matrix into one of two defined categories on the basis of presence or absence of a given feature of interest from said set of descriptors and repeating such analysis until each member of said mixture has been identified in terms of presence or absence of each feature of interest from said set of descriptors and assigned to a terminal node;

(f) a data storage process; and (g) an output process for visually displaying, using computer graphics, a relationship of said descriptors with said mixture objects and classes.

7. A computer-based method of encoding mixture features of planned mixtures or of inadvertent mixtures, or of a combination of planned or inadvertent mixtures, and of identifying and correlating individual said features to a response characteristic that is a trait of interest of the mixture object, wherein said mixture object is in a data set that is characterized in being a mixture of mixture object classes, each class containing one or more of said mixture objects, and wherein multiple mixture objects present a same trait of interest, but classes of mixture objects produce the response characteristic which is a trait of interest through different underlying mechanisms, comprising the steps of:

(a) assembling a set of descriptors and converting said set of descriptors into the form of a bit string such that each descriptor reflects the presence or absence of a potentially useful feature of interest in a mixture object of interest;

(b) examining each mixture object for presence or absence of each of said descriptors;

(c) assembling the results of step (b) into a vector for each mixture object, noting the presence or absence of each feature in said data object;

(d) assembling all vectors generated in step (c) into a matrix with each row corresponding to a mixture object and each column corresponding to a feature;

(e) dividing the mixture objects in said matrix into two defined daughter nodes on the basis of presence or absence of a given feature of interest from said set of descriptors; and (f) repeating step (e) until each mixture object of said matrix has been identified in terms of presence or absence of given features of interest from said set of descriptors and assigned to a terminal node.

8. A computer-based apparatus system for allowing a user thereof to encode features of planned mixtures or of inadvertent mixtures, or of a combination of planned or inadvertent mixtures, and to identify and correlate individual said features to a response characteristic that is a trait of interest of the mixture object, applicable to mixture objects in a data set that is characterized in being a mixture of mixture object classes, each class containing one or more of said mixture objects, and wherein multiple mixture objects present a same trait of interest, but classes of mixture objects produce the response characteristic that is a trait of interest through different underlying mechanisms, comprising:

(a) input means responsive to operator commands enabling an operator to specify a set of descriptors that are subsequently converted into a bit string, such that each descriptor reflects the presence or absence of a potentially useful feature of interest in a mixture object of interest;

(b) storage means for storing the assembled set of (a);

(c) memory means for executing programmed steps that examine each mixture object for presence or absence of each of said descriptors;

(d) means for assembling the results of (c) into a virtual matrix with each row corresponding to a mixture object and each column corresponding to a feature;

(e) means for assigning each mixture object in said matrix recursively into one of two defined categories on the basis of presence or absence of a given feature of interest from said set of descriptors and repeating such analysis until each mixture object of said matrix has been classified in terms of presence or absence of given features of interest from said set of descriptors and assigned to a terminal node; and (f) output means for visually displaying, using computer graphics, the relationships of said descriptors with said mixture objects and classes.

9. A computer software system having a set of instructions for controlling a general purpose digital computer in performing a desired function comprising:

a set of instructions formed into each of a plurality of modules, each module comprising:

(a) an input process responsive to operator commands enabling an operator to specify a set of descriptors and convert said descriptors into a bit string such that each descriptor reflects the presence or absence of a potentially useful feature of interest in a mixture object of interest, wherein each mixture object is a member of a data set that is characterized in being a mixture of classes, each class containing one or more of said mixture objects, and wherein multiple mixture objects present the same trait of interest, but classes of mixture objects produce the response characteristic that is a trait of interest through different underlying mechanisms;

(b) a data storage process for storing the assembled set of (a);

(c) a computational process for executing programmed steps that examine each mixture object of said matrix for presence or absence of each of said descriptors;

(d) a computational process for assembling the results of (c) into a vector for each mixture object and a virtual matrix with each row corresponding to a mixture object and each column corresponding to a feature;

(e) a computational process for assigning each mixture object in said matrix into one of two defined categories on the basis of presence or absence of a given feature of interest from said set of descriptors and repeating such analysis until each member of said matrix has been classified in terms of presence or absence of given features of interest from said set of descriptors and assigned to a terminal node;

(f) a data storage process; and (g) an output process for visually displaying, using computer graphics, a relationship of said descriptors with said mixture objects and classes.

10. A computer-based method of analyzing biological potency of individual chemical structure features out of a plural mixture of chemical compounds wherein a created data set is characterized in being a mixture of data objects, each data object itself being a mixture of active and/or inactive chemical compounds, which active chemical compounds exhibit a trait of interest, wherein the underlying mechanisms of activity may be through a single or multiple mechanisms, comprising the steps of:

(a) assembling a set of descriptors such that each descriptor captures a chemically useful feature of one or more members of a mixture of chemical compounds such that one member is captured if individual chemical compounds are being decoded, two members are captures if pairs of chemical compounds are being decoded, three members are captured if triples of chemical compounds are being decoded and so on;

(b) examining each member, pair or triple, or so forth, of said mixture of chemical compounds for presence or absence of each of said features of interest;

(c) assembling the results of step (b) into a descriptor vector;

d) comparing the features of the individual compound, pair, triple and so forth, to the features of a terminal node of choice and determining a resident terminal node;

(e) repeating step (d) until each compound, pair, triple and so forth of said set of mixtures of chemical compounds has been identified and characterized in relation to the terminal node it would reside within.

11. The method as claimed in claim 1, including the additional step of assembling a chemical structure data file.

12. The method as claimed in claim 1, including the additional step of assembling biological data pertaining to each chemical mixture or mixture of chemicals and assigning each chemical mixture its biological data.

13. The method as claimed in claim 1, in which said correlation is between presence or absence of one or more chemical descriptors and biological activity of a chemical mixture.

14. The method as claimed in claim 1, in which said correlation is between presence or absence of one or more chemical descriptors and pharmacological activity of a chemical compound.

15. The method as claimed in claim 1, including the additional step of determining structure-activity relationships, such relationships comprising sets of rules defining the sets of features specific to each activity class.

16. The method as claimed in claim 1, in which said descriptor is an atom pair.

17. The method as claimed in claim 1, in which said descriptor is an atom triple.

18. The method as claimed in claim 17, in which said atom triple is a set of three defined atoms in a molecule of interest, each atom defined by element, by spatial relation to each of the other two atoms, and by the type of chemical bond or number of chemical bonds separating them in the molecule.

19. The method as claimed in claim 1, in which said descriptor is a molecular fragment.

20. The method as claimed in claim 1, in which said descriptor is a molecular topological torsion.

21. The method as claimed in claim 1, in which said descriptor is a measure of thermodynamic stability.

22. The method as claimed in claim 1, in which said descriptor is a binary of continuous variable.

23. The method as claimed in claim 1, in which said descriptor is a combination in any order of an atom pair, an atom triple, a molecular fragment, a molecular topological torsion, thermodynamic stability or a binary of a continuous variable.

24. The method as claimed in claim 1, in which each descriptor is an element of a vector in said matrix.

25. The method as claimed in claim 1, in which presence or absence of each feature of interest is represented as a 1 or a 0, respectively.

26. The method as claimed in claim 24, in which said vector is computationally represented as a bit string data file.

27. The method as claimed in claim 26, in which said bit string data file is utilized to computationally create a bit string data file.

28. The method as claimed in claim 26, in which said bit string is computationally compressed into a sparse matrix.

29. The method as claimed in claim 28, in which said sparse matrix is statistically analyzed by recursive partitioning.

30. The method as claimed in claim 29, in which said recursive partitioning is performed by the CART method.

31. The method as claimed in claim 29, in which said recursive partitioning is performed by the FIRM method.

32. The method as claimed in claim 29, in which said recursive partitioning is performed by the C4.5 method.

33. The method as claimed in claim 31, in which said FIRM method is converted from multiway splits to binary splits.

34. The method as claimed in claim 1, including the additional step of selecting the descriptor that optimally divides said rows of said data matrix into two subsets of rows, being either compounds or mixtures of compounds where said feature of interest is present or absent, respectively, and repeating this process through subsequent iterations until all descriptors in said descriptor set have been examined repeatedly and all said rows assigned to terminal nodes.

35. The method as claimed in claim 1, in which the result of said recursive partitioning is graphically represented as a recursive partitioning analysis tree.

36. The method as claimed in claim 1, in which said data objects are discrete compounds.

37. The method as claimed in claim 4, in which said data objects are mixtures of discrete compounds.

38. A computer-based method of encoding, decoding and identifying individual chemical compounds out of a chemical mixture, comprising the steps of:
   (a) assembling the results of previously conducted screening of the chemical mixture for a biological activity of interest;
   (b) assembling a set of descriptors such that each descriptor captures a chemically useful feature of one or more members of a chemical mixture;
   (c) examining each combination of members of said chemical mixture for presence or absence of each of said descriptors;
   (d) correlating presence or absence of said chemical descriptors with an assigned terminal node, thereby identifying predicted activity; and
   (e) analyzing subsequent chemical mixtures for chemical structure, comparing their chemical structure against said predicted activity and extrapolating biological reactivity of such subsequent chemical mixtures therefrom.

39. The method as claimed in claim 38, including the additional step of assembling a chemical structure data file.

40. The method as claimed in claim 38, including the additional step of assembling biological data pertaining to each chemical compound and assigning each chemical compound or mixture its biological data.

41. The method as claimed in claim 38, in which said correlation is between presence or absence of one or more chemical descriptors and biological activity of a chemical compound or mixture.

42. The method as claimed in claim 38, in which said correlation is between presence or absence of one or more chemical descriptors and pharmacological activity of a chemical compound or mixture.

43. The method as claimed in claim 38, in which said descriptor is an atom pair.

44. The method as claimed in claim 38, in which said descriptor is an atom triple.

45. The method as claimed in claim 44, in which said atom triple is a set of three defined atoms in a molecule of interest, each atom defined by element, by spatial relation to each of the other two atoms, and by the type of chemical bond or number of chemical bonds separating them in the molecule.

46. The method as claimed in claim 38, in which said descriptor is a molecular fragment.

47. The method as claimed in claim 38, in which said descriptor is a molecular topological torsion.

48. The method as claimed in claim 38, in which said descriptor is a binary of continuous variables.

49. The method as claimed in claim 38, in which said descriptors are a combination in any order of atom pairs, atom triples, molecular fragments, molecular topological torsions, thermodynamic stability descriptors or a binary of continuous variables.

50. The method as claimed in claim 38, in which presence or absence of each feature of intererest is represented as a 1 or a 0, respectively.

51. The method as claimed in claim 38, in which said vector is computationally represented as a bit string.

52. The method as claimed in claim 38, including the additional step of decoding the chemical compounds in said chemical mixture by reference to said matrix vectors for the mixture.

53. The method as claimed in claim 38, in which said recursive partitioning is graphically represented as a recursive partitioning analysis tree.

54. A computer-based method of encoding, identifying and correlating individual genetic features of a genetic polymorphism out of a plural populational mixture of individual subjects so as to identify useful diagnoses and therapies of individuals and in the identification of genes and gene products useful in defining biological targets of interest, comprising the steps of:
   (a) assembling a set of descriptors such that each descriptor captures a genetically useful feature, allele, alleles, or marker, of one or more members of a mixture population of individuals having a phenotype of interest;
   (b) examining each member of said population of individuals for presence or absence of each of said genetic features;
   (c) assembling the results of step (b) into a matrix;
   (d) dividing the data in said matrix into one of two defined categories on the basis of presence or absence of a given genetic features from said set of genetic features;
   (e) repeating step (d) until each member of said population of individuals has been identified and characterized in terms of presence or absence of each genetic feature; and
   (f) correlating presence or absence of said genetic features with known phenotypes of each of said mixture population of individuals, thereby deriving a relationship between genotype and phenotype, said relationship useful in diagnosis and therapy of individuals and also useful for identification of gene products, said gene products useful for selecting drug targets or said gene products useful for determining the genetic origiSn of a disease.

55. The method as claimed in claim 54, including the additional step of assembling a populational phenotype data file.

56. The method as claimed in claim 54, in which said descriptor is an identified allele or marker.

57. The method as claimed in claim 54, in which said descriptor is absence of a given allele or marker.

58. The method as claimed in claim 54, in which each descriptor is an element of a vector in said matrix.

59. The method as claimed in claim 54, in which each individual in said population is encoded by a vector in said matrix.

60. The method as claimed in claim 54, in which presence or absence of each descriptor is represented as a 1 or a 0, respectively.

61. The method as claimed in claim 54, in which said matrix vector is computationally represented as a bit string.

62. The method as claimed in claim 54, in which said bit string is utilized to computationally create a bit string data file.

63. The method as claimed in claim 54, in which said bit string is computationally compressed as a sparse matrix.

64. The method as claimed in claim 54, in which said sparse matrix is statistically analyzed by recursive partitioning.

65. The method as claimed in claim 54, in which said recursive partitioning is performed by the CART method.

66. The method as claimed in claim 54, in which said recursive partitioning is performed by the FIRM method.

67. The method as claimed in claim 54, in which said recursive partitioning is performed by the C4.5 method.

68. The method as claimed in claim 54, in which said FIRM method is converted from multiway splits to binary splits.

69. The method as claimed in claim 54, including the additional step of selecting the descriptor that correlates most closely with the highest average incidence of a phenotype of interest of all individuals in the population that have such a descriptor and creating two subsets of individuals where said descriptor is present or absent, respectively, and repeating this process through subsequent iterations until all descriptors in said descriptor set have been examined and analyzed for prevalence in said population.

70. The method as claimed in claim 54, including the additional step of decoding the individuals in said population by reference to said matrix vectors.

71. The method as claimed in claim 54, in which said recursive partitioning is graphically represented as a recursive partitioning analysis tree.

72. The method as claimed in claim 54, in which said statistical test for splitting a node is a t-test.

73. The method as claimed in claim 54, in which said statistical test for splitting a node is a chi-square test.

* * * * *